United States Patent [19]

McRae

[11] Plant 4,333

[45] Nov. 21, 1978

[54] LILY PLANT: LILIUM JULIANA

[75] Inventor: Edward A. McRae, Boring, Oreg.

[73] Assignee: Melridge, Inc., Sandy, Oreg.

[21] Appl. No.: 865,012

[22] Filed: Dec. 27, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant, bearing large clusters of medium-sized flowers of excellent form, unusual color, and long persistence, both on the plant and as cut flowers. Buds of the new plant show a soft buff color when the tepals divide and unfurl, and the upright flowers are particularly characterized by their creamy-white color, which is completely new in the upright and outfacing Asiatic divisions of lilies. Both plant and flower are characterized by high disease resistance and high tolerance of infection by virus. The bulbs may be precooled and forced for cut flowers. The clone is very vigorous and is a good grower and propagator.

1 Drawing Figure

BACKGROUND OF THE INVENTION

My new variety of lily plant originated as a seedling selected from a group of seedlings at Gresham, Oreg. The seedlings were planted during a breeding program carried on by me since the year 1965. This program has as its primary objective the production of upright hybrid Asiatic lilies in white and cream color shades heretofore unknown in lily breeding; also to be characterized by plant vigor, rapid propagation, high resistance to disease, tolerance of infection by virus, having flowers of superior form and color.

I achieved the desired objective by using as the seed parent a clone selected from the complex hybrid strain, Lilium 'Hallmark'. The pollen parent was produced by pollinating an unspotted clone of *Lilium dauricum* with the pollen of a different clone from the complex hybrid Lilium 'Hallmark' strain.

My new lily plant is characterized by a clear creamy-white color. It shows vigorous growth and propagation characteristics. Its stems are dark in color and provide an attractive contrast to the abundant foliage, which is deep green in color with a reddish cast.

The plant has a large number of buds, producing from 6 to 10 from a bulb 5 to 7 inches in circumference. The buds are an attractive soft buff color when the tepals first divide, and the inner tepals are a creamy white with soft buff throat. The flower becomes a pure, sparkling white on the second day after opening.

The flowers are particularly distinctive. They are characterized by tepals of fine form, unusual breadth, and sharp, clean outline. They are lightly spotted, primarily at the base, and are a sparkling, enduring white because of their great thickness. The pollen of this new lily is a fluorescent tangerine red, providing contrast to its unusual color.

The plant is one of the most vigorous upright Asiatic lilies yet produced. It is a rapid propagator and has superb disease resistance and a high degree of tolerance of infection by virus. It is an excellent garden lily and is outstanding for use in the cut flower or pot plant trade by forcing precooled bulbs, all as observed at Gresham, Oreg.

My new variety of lily plant has been asexually reproduced by me and under my direction at Gresham, Oreg. Successive generations produced by bulb scale propagation and natural propagation from bulblets have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing which shows the plant, its stem and foliage, its buds in their various stages of development, and the open bloom in full color. Also shown is the tepal arrangement, the great width of the tepals, the connection of the flower to the stalk, the compact inflorescence, and particularly the unusual creamy-white color of the flower.

DESCRIPTION OF THE NEW VARIETY

The following is a detailed description of my new variety of Asiatic hybrid lily, with nomenclature according to *The International Lily Register* (Royal Horticultural Society, London, 2nd edition, 1969) and with color designations according to the Royal Horticultural Society Color Chart, published by the Royal Horticultural Society in 1966.

THE PLANT

Origin: Seedling.

Parentage:

*Seed parent.*—Lilium × 'Hallmark' clone (unpatented).

*Pollen parent.*—Spotless form of *Lilium dauricum* × Lilium 'Hallmark' clone (unpatented).

Classification:

*Botanic.*—Hybrid Lilium cultivar; Division I-A of the Horticultural Classification of Lilies of the R.H.S.

*Commercial.*—Asiatic hybrid lily.

Form: Single stem, tall and stately.

Height: 20 to 25 inches from bulbs of 5 to 7 inch circumference.

Growth: Very vigorous and upright with exceptional strength.

Foliage:

*Quantity.*—Abundant.

*Size of leaf.*—3 to 4 inches long.

*Shape of leaf.*—Lanceolate.

*Texture.*—Leathery glossy.

*Color.*—Deep green on both upper and under sides.

Bulbs:

*Shape.*—Ovoid.

*Size.*—Any size, ranging up to about 12 inches in circumference.

*Color.*—White, with a yellowish cast when exposed to light.

THE BUD

Form: Obtuse; urn-shaped and long.

Size: About 3 inches long and 1 to 2 inches in circumference, increasing as bud develops.

Opening: Bud opens slowly.

Color: Soft buff outerside of tepals when tepals first divide. Inside of flower a creamy-white with soft buff throat when tepals first unfurl; color changes to pure white on second day after opening.

Tepals: The tepals curl back. They are creamy-white on the inside and soft buff on the outside.

Peduncle: About 2 inches long; slightly hairy; erect; deep green in color.

THE FLOWER

Blooming habit: Recurrent. Annually in mid season. Blooms once and profusely.

Size: Medium; about 5 inches in diameter.

Borne: In clusters, from 6 to 10 on a single stem, from a bulb 5 to 7 inches in circumference.

Shape: Cup-shaped. The tepals recurve slightly as the bloom matures.

Tepalage:

*Number of tepals.*—6.

*Arrangement.*—Imbricated.

*Color.*—Inner sides of tepals RHS 158 C through D, with RHS 27 C throat, upon first opening. Color lightens to RHS 155 A on second day after opening. Outer side of tepals is RHS 27 A through C.

*Tepal longevity.*—Tepals stay on the stem about 3 weeks.

*Spotting.*—Lightly spotted with small spots at the base of the tepals.

Pedicel:

*Length.*—About 2 inches.

*Color.*—Deep green.

*Form.*—Sturdy and upright.

Color change: The creamy-white color of the flower changes to a clear white on the second day after opening.

Appearance: The flower is shiny.

Disease resistance: The flower and plant are highly resistant to disease; in particular, they are resistant to Fusarium and Botrytis.

Fragrance: The flower is not fragrant.

Lasting quality: The flower is long lasting on the plant and exceptionally long lasting as a cut flower.

THE REPRODUCTIVE ORGANS

Stamens, anthers:

*Arrangement.*—Typical of Liliaceae.

*Length.*—About 2 inches.

*Number.*—6.

*Filaments.*—Length, about 2 inches; color, cream and greenish at base.

Pollen and Anthers: Brilliant tangerine-red.

Pistils: One in number with a length of about 2 inches.

Stigma: Deepest purple in color.

Characteristics of ovaries: Typical of genus Lilium.

THE FRUIT

Fertility: The fruit is fertile.

Shape: The fruit is ovoid.

Color at maturity: The fruit is soft parchment brown.

My new variety of Asiatic hybrid lily most nearly resembles the variety 'Sterling Star' (unpatented) but is distinguished therefrom by its more compact plant stature; its broader leaves; the improved form of its flowers, with broader and thicker tepals which emphasize its clear white color; its increased longevity of flowers; its more compact inflorescence; its greater resistance to leaf and flower scorch, which make it a much superior plant when produced from precooled bulbs forced for cut flowers.

I claim

1. A new and distinctive variety of Asiatic hybrid lily plant substantially as herein shown and described, characterized by its compact inflorescence of flowers of excellent form, with exceptionally thick and broad tepals; by the exceptional longevity of its flowers, both on the plant and as cut flowers; by its strong stem and abundant, dark green foliage; by its rapid propagation characteristics; its superb disease resistance; its high tolerance to virus; and its suitability for use both as a garden flower and as a cut flower produced by forcing precooled bulbs; and in particular by its clear, creamy-white color, which is unique in the hybrid Asiatic division of upright lilies suited for forcing.

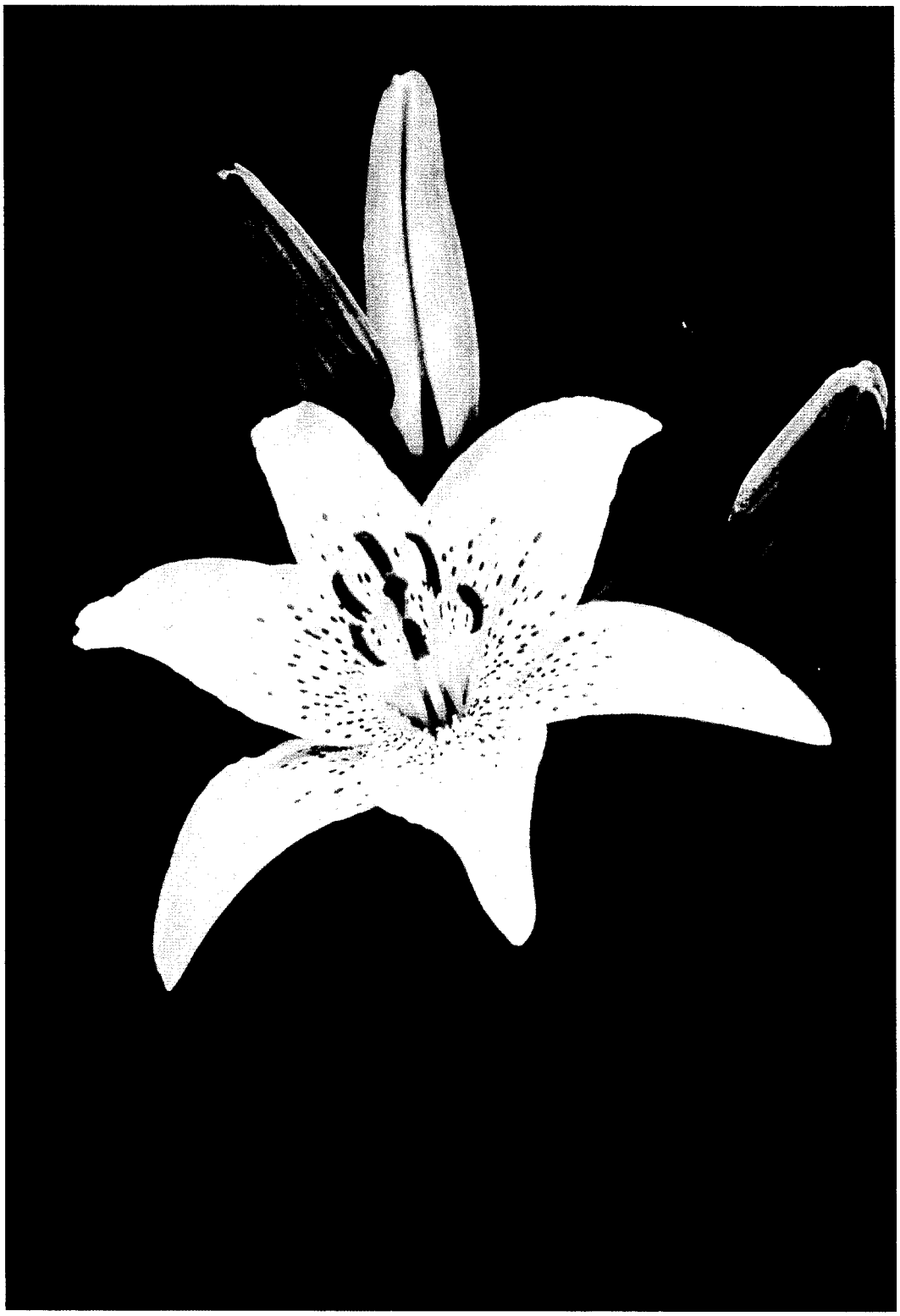

* * * * *